United States Patent
Lu et al.

(10) Patent No.: US 12,080,426 B2
(45) Date of Patent: Sep. 3, 2024

(54) FUNCTIONAL DEEP NEURAL NETWORK FOR HIGH-DIMENSIONAL DATA ANALYSIS

(71) Applicant: University of Florida Research Foundation, Inc., Gainesville, FL (US)

(72) Inventors: Qing Lu, Gainesville, FL (US); Shan Zhang, Gainesville, FL (US); Tingting Hou, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 440 days.

(21) Appl. No.: 17/217,082

(22) Filed: Mar. 30, 2021

(65) Prior Publication Data

US 2021/0313065 A1 Oct. 7, 2021

Related U.S. Application Data

(60) Provisional application No. 63/005,563, filed on Apr. 6, 2020.

(51) Int. Cl.
| | |
|---|---|
| *G16B 20/00* | (2019.01) |
| *G06N 3/04* | (2023.01) |
| *G06N 3/08* | (2023.01) |
| *G06T 7/00* | (2017.01) |
| *G16B 5/20* | (2019.01) |
| *G16H 10/60* | (2018.01) |
| *G16H 30/40* | (2018.01) |
| *G16H 50/20* | (2018.01) |
| *G16H 50/30* | (2018.01) |

(52) U.S. Cl.
CPC ............... *G16H 50/20* (2018.01); *G06N 3/04* (2013.01); *G06N 3/08* (2013.01); *G06T 7/0012* (2013.01); *G16B 5/20* (2019.02); *G16H 10/60* (2018.01); *G16H 30/40* (2018.01); *G16H 50/30* (2018.01); *G06T 2207/20081* (2013.01); *G06T 2207/20084* (2013.01); *G06T 2207/30016* (2013.01)

(58) Field of Classification Search
CPC .................................. G16H 50/20; G16B 5/20
See application file for complete search history.

(56) References Cited

U.S. PATENT DOCUMENTS

| | | | | |
|---|---|---|---|---|
| 11,514,289 B1 * | 11/2022 | Otte | ........................ | G06N 20/00 |
| 11,538,555 B1 * | 12/2022 | Hamp | ..................... | G16B 5/20 |

(Continued)

*Primary Examiner* — Reginald R Reyes
(74) *Attorney, Agent, or Firm* — Thomas | Horstemeyer, LLP

(57) ABSTRACT

Various examples of methods and systems are provided related to functional deep neural networks (FDNNs), which can be used for high dimensional data analysis. In one example, a FDNN can be trained with a training set of omic data to produce a trained FDNN model. The likelihood of a condition can be determined based upon output indications of the FDNN corresponding to the one or more phenotypes, with the output indications based upon analysis of omic data including a multi-level omic profile from an individual by the trained FDNN. The FDNN model can include a series of basis functions as layers to capture complexity between the omic data with disease phenotypes. A treatment or prevention strategy for the individual can be identified based at least in part upon the likelihood of the condition.

17 Claims, 7 Drawing Sheets

(56) References Cited

U.S. PATENT DOCUMENTS

2011/0059090 A1* 3/2011 Revets .................. C07K 16/32
                                                    435/69.6
2021/0174958 A1* 6/2021 Drake .................... G06N 20/10

* cited by examiner

FUNCTIONAL DEEP NEURAL NETWORK FOR HIGH-DIMENSIONAL DATA ANALYSIS

CROSS REFERENCE TO RELATED APPLICATIONS

This application claims priority to, and the benefit of, co-pending U.S. provisional application entitled "Functional Deep Neural Network for High-Dimensional Data Analysis" having Ser. No. 63/005,563, filed Apr. 6, 2020, which is hereby incorporated by reference in its entirety.

STATEMENT REGARDING FEDERALLY SPONSORED RESEARCH OR DEVELOPMENT

This invention was made with government support under Grant Numbers R01 LM012848 and R01 DA043501 awarded by the National Institutes of Health. The government has certain rights in the invention.

BACKGROUND

The concept of treating diseases with precise interventions, designed rationally from a detailed understanding of the disease etiology and individual differences, has been widely accepted as the goal of precision medicine. Toward that end, there is an expectation that human genome discoveries will revolutionize the current trial-and-error practice of medicine by enabling more accurate disease prediction and precise prevention/treatment strategies. The use of emerging findings from omic studies and other existing knowledge to predict disease risk is an important step towards the goal of precision medicine.

SUMMARY

Aspects of the present disclosure are related to functional deep neural network (FDNN), which can be used for high dimensional data analysis (e.g., omic data analysis). In one aspect, among others, a method for risk prediction using high-dimensional omic data comprises training a functional deep neural network (FDNN) with a training set of omic data to produce a trained FDNN model; determining a likelihood of a condition based upon output indications of the FDNN corresponding to the one or more phenotypes, the output indications based upon analysis of omic data comprising a multi-level omic profile from an individual by the trained FDNN; and identifying a treatment or prevention strategy for the individual based at least in part upon the likelihood of the condition. The FDNN model comprises a series of basis functions as a plurality of layers to capture complexity between the omic data with disease phenotypes, the training set of omic data comprising biomarkers applied as inputs to the FDNN and one or more phenotypes. A first layer of the plurality of layers can comprise a univariate function and remaining layers of the plurality of layers comprise a bivariate function.

In various aspects, the training set of omic data can comprise risk predictors related to the one or more phenotypes, the risk predictors including biomarkers or established risk predictors. The one or more phenotypes can comprise disease diagnostic assessments, multiple correlated phenotypes, or high-dimensional phenotypes. The high- dimensional phenotypes can comprise biomarkers or neuroimaging data. In one or more aspects, the plurality of layers of the FDNN can be built via functional linear models with functional coefficients as weights in individual layers. The plurality of layers of the FDNN can adopt a penalty on a second-order derivative of the basis functions to ensure smoothness of the basis functions. Weights and biases in the FDNN can be functions, and the FDNN can take an integral of functional coefficients in individual layers.

In another aspect, a system for risk prediction using high-dimensional omic data comprises at least one computing device comprises processing circuitry including a processor and memory; and a FDNN analysis program that, when executed by the processing circuitry, cause the at least one computing device to: receive an omic profile of an individual; determining a likelihood of a condition based upon output indications of a functional deep neural network (FDNN) corresponding to one or more phenotypes, the output indications based upon analysis of omic data comprising the multi-level omic profile by the FDNN, where the FDNN was trained with a training set of omic data to produce a trained FDNN model, the FDNN model comprising a series of basis functions as a plurality of layers to capture complexity between the omic data with disease phenotypes; and providing a treatment or prevention strategy identified for the individual based at least in part upon the likelihood of the condition. A first layer of the plurality of layers can comprise a univariate function and remaining layers of the plurality of layers comprise a bivariate function.

In one or more aspects, the training set of omic data can comprise biomarkers applied as inputs to the FDNN and the one or more phenotypes. The training set of omic data can comprise risk predictors related to the one or more phenotypes, the risk predictors including biomarkers or established risk predictors. The one or more phenotypes can comprise disease diagnostic assessments, multiple correlated phenotypes, or high- dimensional phenotypes. The high-dimensional phenotypes can comprise multi-level omic or neuroimaging data. In some aspects, the plurality of layers of the FDNN can be built via functional linear models with functional coefficients as weights in individual layers. The plurality of layers of the FDNN can adopt a penalty on a second-order derivative of the basis functions to ensure smoothness of the basis functions. Weights and biases in the FDNN can be functions, and the FDNN can take an integral of functional coefficients in individual layers.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1A:
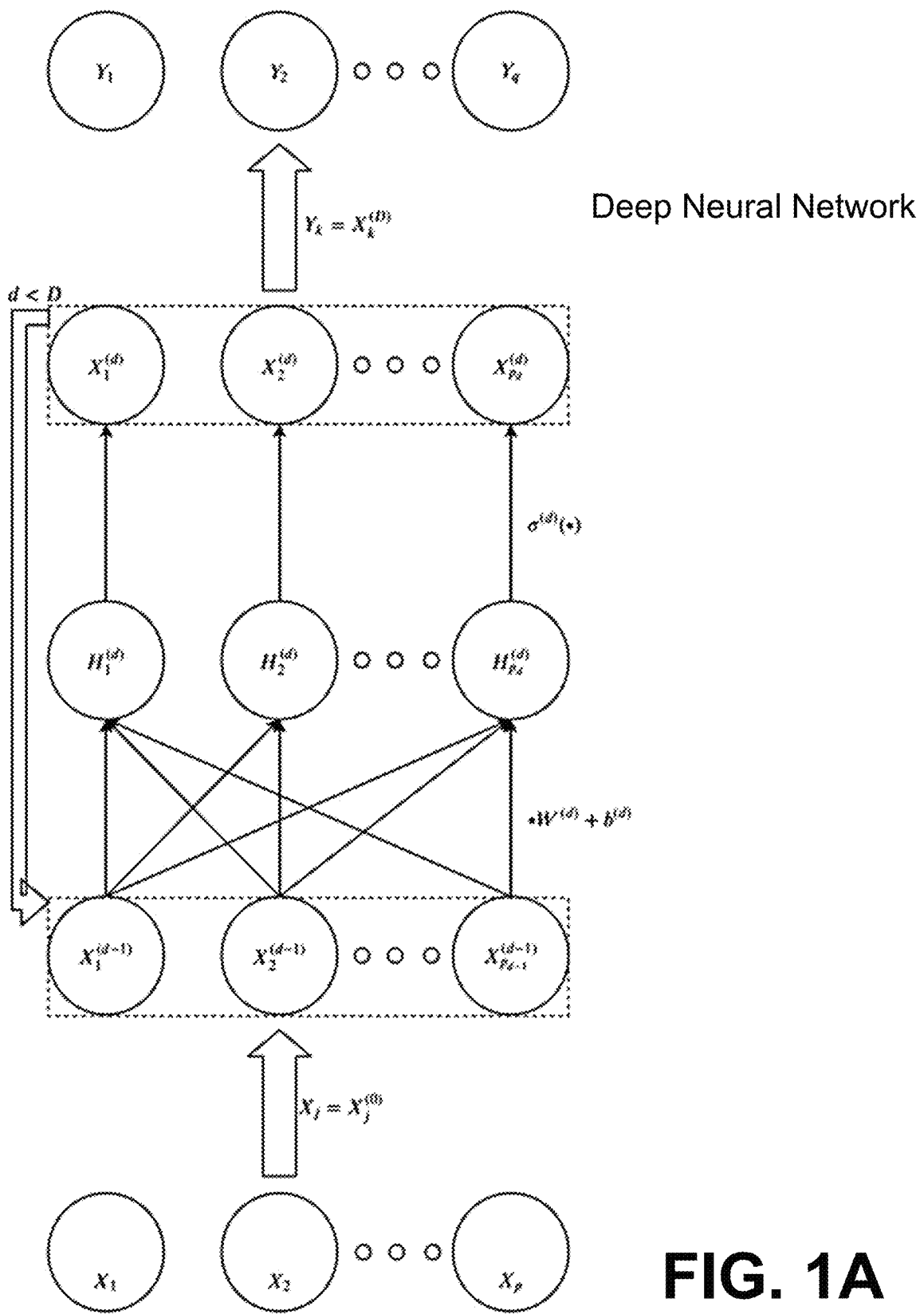
FIGS. 1A and 1B are graphical representations illustrating examples of a deep neural network (DNN) and a deep functional neural network (DFNN), in accordance with various embodiments of the present disclosure.

Disclosed herein are various examples related to a functional deep neural network (FDNN) methodology, which can be used for high dimensional data analysis (e.g., omic data analysis). The progress of precision medicine is driven by new technologies, including the Artificial Intelligence (AI) technology, that can integrate disease-related information (e.g., individuals' multi-omic profiles) for accurate disease prediction and precise prevention. FDNN is a new AI tool that can be utilized in a wide range of applications such as, but not limited to, the identification and diagnosis of the condition of individuals. The effective use of the FDNN is demonstrated in examples related to genetic risk prediction of nicotine dependence and identification of risk predictors for early detection of Alzheimer's disease. Reference will now be made in detail to the description of the embodiments as illustrated in the drawings, wherein like reference numbers indicate like parts throughout the several views. In the description, well known components, methods, and/or processing techniques are omitted or briefly described so as not to obscure the concepts being presented. As used herein, the "present disclosure" refers to any one of the examples described herein and any equivalents. Furthermore, reference to various feature(s) of the "present disclosure" is not to suggest that all examples must include the referenced feature(s).

Some aspects of the present disclosure can be implemented by software executed by personal computers or clusters equipped with CPUs or GPUs, as described and illustrated. As would be apparent to one having ordinary skill in the art, the present disclosure may be implemented, at least in part, by computer-readable instructions in various forms, and the present disclosure is not intended to be limiting to a particular set or sequence of instructions executed by the processor.

The examples described herein are not limited in application to the details set forth in the following description or illustrated in the drawings. Examples presented in the present disclosure are capable of being practiced or carried out in various ways. Also, the phraseology and terminology used herein is for the purpose of description and should not be regarded as limiting. The use of "including," "comprising," or "having" and variations thereof herein is meant to encompass the items listed thereafter, additional items, and equivalents thereof. The terms "connected" and "coupled" are used broadly and encompass both direct and indirect connections and couplings. In addition, the terms "connected" and "coupled" are not limited to electrical, physical, or mechanical connections or couplings. As used herein the terms "machine," "computer," "server," and "work station" are not limited to a device with a single processor, but may encompass multiple devices (e.g., computers) linked in a system, devices with multiple processors, special purpose devices, devices with various peripherals and input and output devices, software acting as a computer or server, and combinations of the above.

With the recent advancement in high-throughput technologies, genome-wide association studies (GWAS) and omic (e.g., epigenomic, transcriptomic and proteomic) studies have been commonly adopted to uncover new biomarkers predisposing to common complex diseases. During the past decade, thousands of variants have been identified through GWAS and omic studies, some with compelling biological plausibility for a role in disease etiology. Despite such success, for most complex diseases, identified genetic variants are associated with small effect size and only explained a small fraction of total heritability. Many common diseases are influenced by the interplay of multiple genes and other risk factors (such as environmental determinants) in a complex manner. This complexity, however, has not been taken fully into account by many existing tools, which often assumes biomarkers related to disease phenotypes in an additive and linear manner. By not considering the complex genetic interplay, the effectiveness in accurately predicting and diagnosing individual conditions can be significantly limited.

AI methods, such as deep neural networks (DNN), hold great promise for risk prediction analysis of complex diseases. Based on the hierarchy of the neural network framework, DNN learns complicated features from simpler ones, making it capable of capturing non-linear and non-additive effects. With these appealing features and great performance, DNN can be used in omics, especially in the fields of regulatory genomics, variant calling and pathogenicity scores. Despite successful application in these areas, the use of DNN in revealing the complex relationships between biomarkers and common diseases is still limited.

DNN can be utilized for building precise risk prediction models for complex human diseases (e.g., Alzheimer's disease). Risk prediction models can use human genome discoveries and other established risk factors to identify high-risk subpopulations so that appropriate prevention/treatment strategies can be applied early to reduce morbidity and mortality. While promising, the high-dimensional omic data (e.g., thousands of variants) and complex omic structure bring tremendous challenges to use DNN in current risk prediction research. Most variants have small or no effect on diseases, and fitting DNN on a large number of predictors without considering the underlying omic structure (e.g., linkage disequilibrium) can result in a severe overfitting issue.

While a vast amount of available omic data offers great potential in risk prediction analysis of complex diseases, the high dimensionality of the omic data and the complexity of omic structure bring tremendous analytic challenges. The high-throughput technology allows for the simultaneous evaluation of the role of thousands or even millions of variants in complex diseases. Nevertheless, fitting a DNN on such a large number of biomarkers could bring a serious overfitting issue as previously noted. Linkage disequilibrium (LD) exists among neighboring variants and disease-associated variants are often in a LD block. Considering the underlying structure can help combat the overfitting issue.

Moreover, different types of disease phenotypes are often collected in a study. Besides the measurement of a disease, which is typically a scalar variable, researchers are sometimes interested in studying a vector of phenotype variables (e.g., the progression of disease measured over time). With the rapidly evolving technologies and ever-decreasing cost, studies are starting to collect multi-level omics data and imaging data, which are often high-dimensional and stored as matrices or tensors. While multi-level omics and imaging data provide a great opportunity to study complex disease (e.g., using them as intermediate phenotypes), few methods are currently available for high-dimensional risk prediction analysis of complex phenotypes (e.g., vectors and matrices) with the consideration of non- linear and non-additive effects.

Formed risk prediction models can be used to successfully identify high-risk subpopulations, so that appropriate prevention/treatment strategies can be used to reduce morbidity and mortality. Identifying biomarkers can help in early detection of diseases and promote the development of effective treatment strategies. To address these challenges and facilitate the high-dimensional risk prediction analysis of complex diseases, a functional deep neural network (FDNN) is proposed that inherits the strengths from both DNN and the function linear model (FLM). FLM is a popularly used method in functional data analysis (FDA), which deals with data in the form of functions. FLM can be used to analyze data measured over time and can be used in high-dimensional data analysis, such as omic data analysis and imaging data analysis. Specifically, with the high-dimensional omic data as the input layer and various types of phenotypes as the output layer, the proposed FDNN first fits a series of basis functions to each layer respectively. The series of basis functions can model high-dimensional omic data and complex disease phenotypes, considering their underlying structure. The FDNN further builds multiple hidden layers via functional linear models with functional coefficients as weights for the hidden nodes. The multi-layer functional neural network can capture the complex relationship between omic predictors and disease phenotypes.

The FDNN has a number of attractive features: 1) it has a built-in facility to account for the underlying structures of the omic and phenotype data (e.g., LD), which helps capture disease-related variants and overcome the curse of dimensionality; 2) similar as DNN, it uses multi-layer functional neural network to model the complex relationship between biomarkers and disease phenotypes; and 3) it can be used to analyze different types of disease phenotypes (e.g., scalar, vector, matrix). Through simulations and two real data applications, it can be shown that FDNN outperforms conventional methods, such as DNN and FLM. In fact, at certain conditions, FDNN can be simplified to DNN. In other words, FDNN can be viewed as the generalization of DNN to high-dimensional data with complex phenotypes.

This disclosure presents the idea of a new AI tool, the FDNN method, based on FLM and DNN and uses simulations to compare the performance of FDNN with those of FLM and DNN under various scenarios. The methods are illustrated via real data applications. FDNN is developed based on both FLM and DNN. Two types of FLMs are first introduced to handle different types of outputs. The technical details are provided in Appendix A (Solutions of FLM) below. A short review on DNN is provided, and based on the idea of FLM and DNN, the proposed FDNN is developed. The technical details of FDNN are summarized in the Appendix B (Forward Propagation) and Appendix C (Back Propagation) below.

Functional Linear Model.

FLM for scalar phenotypes. The FLM is briefly introduced in the setting of genetic data analysis with a scalar output. Let $y_i$ and $Z_i = (Z_{i1}, \ldots Z_{im})$ denote the quantitative phenotype and covariates (e.g., gender) for the i-th individual. Assuming p single-nucleotide variants (SNVs) with their corresponding position, the positions can be scaled into [0,1] and the genetic variant function, $G_i(t)$, $t \in [0,1]$ obtained for the i-th individual. Then, the FLM is fit to model the relationship between the scalar output $y_i$ and the functional genetic variable $G_i(t)$ as well as covariates $Z_i$:

$$\hat{y}_i = \theta_0 Z_i \theta + \int G_i(t)\beta(t)dt, \quad (2.1)$$

where $\beta(t)$ is the coefficient function measuring the genetic effects across the genome. The parameters $\theta_0$ and $\theta$ are the intercept and coefficients of the covariates.

FLM for functional phenotypes. For a functional response $Y_i(s_{ij})$, in which $s_{ij}$ means the j-th position for the i-th individual, the following model can be used.

$$\hat{Y}_i(s_{ij}) = Z_i\theta + \alpha_0(s_{ij}) + \int \alpha(s_{ij},t)G_i(t)dt, \quad (2.2)$$

where $\alpha(s,t)$ is a bivariate function, and $\alpha_0(s)$ is a function which plays the role as an intercept.

FLM has many desirable features for high-dimensional genetic data analysis. By considering the effects of SNVs as smooth functions, information from adjacent SNVs (i.e., nearby SNVs tend to have similar effects due to linkage disequilibrium) can be utilized and the number of parameters reduced, which help capture true signals and overcome the curse of dimensionality. Moreover, FLM has its own uniqueness of handling measurement errors and missing data, which is often observed in genetic data analysis. Despite these advantages, FLM is not able to capture non-linear relationships between SNVs and phenotypes, as well as the inter-relationships between SNVs (e.g., interactions). In order to address the issue, the DNN idea is introduced into FLM in order to improve its capacity of modelling complex non-linear and non-additive genetic effects.

Deep Neural Network

A neural network can be viewed as a multi-stage nonlinear regression model.

The model $f_N: \mathbb{R}^p \to \mathbb{R}^q$ can be written in a recursive way:

$$X^{(0)} = [Z, G] \quad (2.3)$$

$$X^{(d)} = \sigma^{(d)}(X^{(d-1)}W^{(d)} + b^{(d)}) \quad (2.4)$$

$$\hat{Y}^{(d)} = f_N(X^{(0)}) = X^{(D)}, \quad (2.5)$$

where $\{\sigma^{(d)}(d), d=1, 2, \ldots, D\}$ are activation functions which map from $\mathbb{R}$ to $\mathbb{R}$.

$\{w^{(d)}(d), b^{(d)}(d), d=1, 2, \ldots, D\}$ are coefficients which can be estimated based on performance criteria defined on the $\hat{Y}$ and Y. $\{X^{(d)}(d), d=1,2, \ldots, D-1\}$ are named as a hidden layer for each d. The elements $\{X^{(d)}_1(d), \ldots, X^{(d)}_{pd}(d)\}$ of each hidden layer are hidden Functional Deep Neural Network In the proposed FDNN approach, G(t) based on SNVs is used to initialize the FDNN. Applying Eq. (2.2) on G(t), the first hidden layer $X^{(1)}$ can be obtained via Eq. (2.6).

$$X^{(1)} = \sigma^{(1)}\left(Z\theta + \alpha_0^{(1)} + \int \alpha^{(1)} G dt^{(0)}\right). \quad (2.6)$$

Then, additional D−1 hidden layers can be built recursively with possibly different functional coefficients as shown in Eq. (2.7).

$$X^{(d)} = \sigma^{(d)}\left(\alpha_0^{(d)} + \int \alpha^{(d)} X^{(d-1)} dt^{(d-1)}\right), 1 < d \leq D. \quad (2.7)$$

The prediction value is shown in Eq. (2.8) or Eq. (2.9) by applying Eq. (2.1) or Eq. (2.2) for scalar phenotypes or functional phenotypes, respectively.

$$\hat{Y} = X^{(D)} \quad (2.8)$$

$$\hat{Y}_k = X^{(D)}(t_k^{(D)}). \quad (2.9)$$

When the output is scalar, $\alpha^{(D)}_0$ is a scalar and $\alpha^{(D)}$ is a univariate function. When the output is a vector, $\alpha^{(d)}_0$ is a univariate function and $\alpha^{(d)}$ is a bivariate function. In a similar manner, the model can be extended to other complex phenotypes (e.g., neuroimaging phenotypes stored in matrices).

Figure 1B:
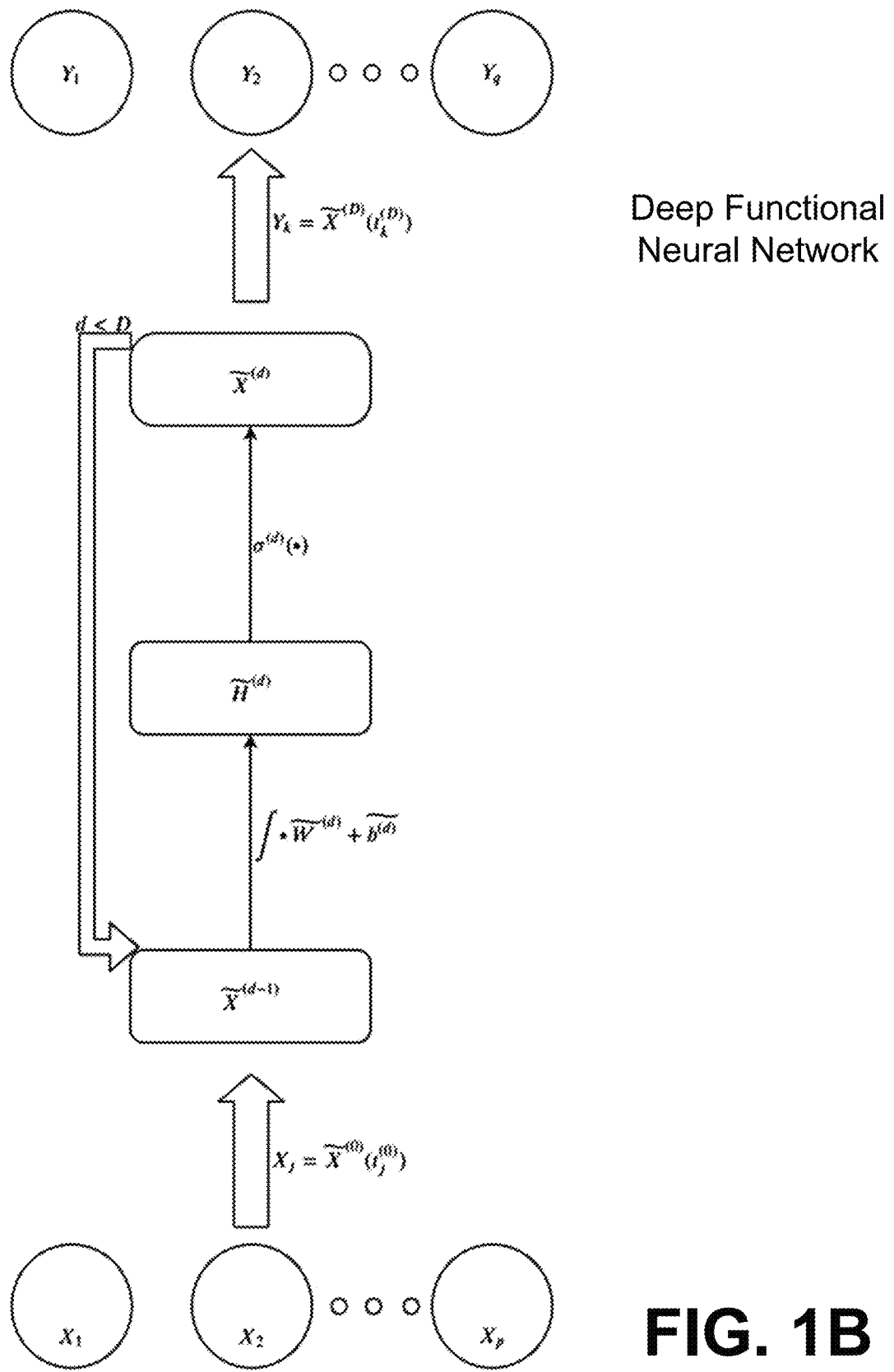

Referring to FIGS. 1A and 1B, shown are graphical representations of a DNN and a DFNN, in accordance with various embodiments of the present disclosure. The illustrations of DNN and DFNN are when the phenotype is functional omitting the covariates. When the phenotype is a scalar, the graph can be adjusted by simply removing $t_k$. Compared with DNN, matrix multiplication can be substituted based on the weight matrix $W^{(d)}$ with integration based on the functional coefficient $\alpha^{(d)}$ in the FDNN model. The key difference between DNN and FDNN lies that the weights $\alpha^{(d)}$ and biases $\alpha_o^{(d)}$ are functions. By treating the weights and biases as functions, the number of parameters can be reduced, and structure of the data can be taken into account. In addition, FDNN addresses the overfitting issue in the high-dimensional data analysis, and can be easily extended for complex phenotypes (e.g., the progression of disease measured over time and neuroimaging phenotypes).

The solution of this model depends on back-propagation method, which is discussed in Appendix C below. It enables the problem to be solved when the time points are not aligned. The problem can be handled when $t_{ij} \neq t_{i'j}$, $i \neq i'$.

Risk prediction models can be used to successfully identify high-risk subpopulations and aid in the appropriate prevention/treatment strategies for an individual to reduce morbidity and mortality. Use of the FDNN can avoid the current trial-and-error practice of medicine by enabling more accurate disease prediction and precise prevention/treatment strategies. By applying FDNN to large-scale datasets, FDNN can form more accurate and robust risk prediction models than other completing methods (e.g., DNN). The model can then be applied to data from individual patients for diagnosis and treatment. For example, omic data from an individual can be analyzed by the trained FDNN to determine a likelihood of a condition. Omic data profiles (or multi-level omic profiles) can include genomic, epigenomic, proteomic, metabolomic and/or microbiomic profiles. The FDNN method and software can facilitate high-dimensional risk prediction modeling and facilitate accurate risk prediction models for complex human diseases or other conditions.

SIMULATION EVALUATION

Data Description. Simulations were conducted to show the advantages of FDNN over existing methods, such as FLM and DNN, in the setting of genetic data analysis. In order to mimic the real structure of genetic data (e.g., allele frequencies and linkage disequilibrium), the genetic data was obtained from the real sequencing data located on Chromosome 17: 7344328 - 8344327 from the 1,000 Genome Project Consortium ("A map of human genome variation from population-scale sequencing" *Nature* 467 (2010), no. 7319, 1061). Specifically, a segment of SNVs, 200 training samples and 50 testing samples were randomly chosen. Due to the intensive computation time of analyzing complex phenotypes, 100 replicates were simulated. Based on the genetic data, different types of phenotypes (i.e., scalars, vectors and matrices) were simulated, and both linear and non-linear relationships between genotypes and phenotypes evaluated.

To reflect the real disease scenarios, random noise was added to the simulated data, and the performance of three methods compared by gradually increasing the noise level. A general form of the simulation model is given below, $$Y_{ik} = Y_i(s_k) = f(s_k; G_i) + \epsilon_{ik}.$$

where $f$ is a function of $s_k$ and is determined by $G_{i\ldots}$. The explicit expression would be given in corresponding simulations. $\epsilon_{ik}$ follows i.i.d normal distribution with mean 0 and the standard deviations of 0.3, 0.6 and 1.2. The explicit expression of the model is given in the following simulations.

Simulation 1. In simulation 1, the performance of three methods were evaluated under different types of phenotypes (i.e., scalar, vector and matrix). For each replicate, 200 training samples and 50 testing samples were randomly chosen, each with 200 SNPs from the 1,000 Genome Project. Based on the genotypes, phenotypes were simulated using the following model, $$f(x; g_j, t_j, j=1, \ldots, 200) = \sum_{i=1}^{20}\sum_{j=1}^{200} c_l g_j^{c_l} B_{1l}(t_j) B_{2l}(x), \quad (3.1)$$

where $B_{1l}$ and $B_{2l}$ are two 4-order B-spline basis functions. They are generated by 10 different random points from $U(0,1)$. $c_i$ are randomly generated from a uniform distribution on $[-2,2]$. $e_i$ are randomly generated from a uniform distribution, $U[1/3,3]$. $Y_i(x)$ has a support of $[0,1]$. In simulation, the function has K points as realizations of the function, and the points are randomly generated from a uniform distribution, $U[0,1]$. When K=1, the $Y_i(x)$ is a scalar. For vector types of phenotype, we set K=20 (i.e., the phenotype of ith individual is a vector of 20 elements) was set. In the matrix setting (e.g., in 2-dimensional space), outer product was applied on two functions in the form of Eq. (3.1). The realized points are randomly generated from a rectangle in $(0,1)\times(0,1)$, where K=1000.

Figure 2:
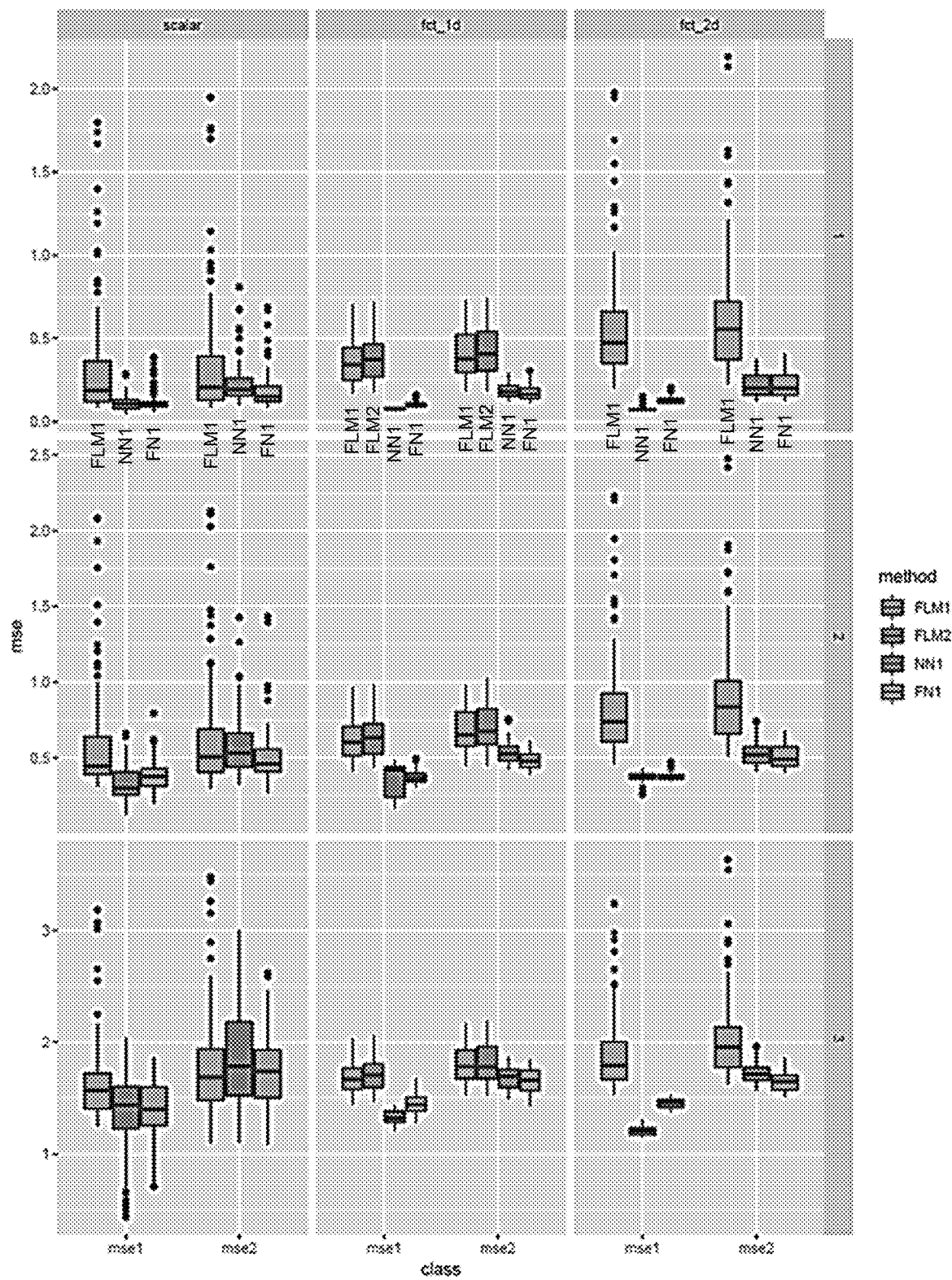
FIGS. 2-4 illustrate examples of simulation results comparing mean squared error (MSE) of the DFNN to other methods, in accordance with various embodiments of the present disclosure.

FIG. 2 summarizes the results from simulation 1. In this simulation, the performance of three methods were compared for three different types of phenotypes (i.e., scalar, vector, and matrix) and three different levels of noise. The left cluster and the right cluster in each panel of FIGS. 1A and 1B present the mean squared error (MSE) of 3 methods calculated from the training data and testing data, respectively. Overall, FDNN attains better or comparable performance than FLM and DNN as demonstrated by the results from the testing data. It was also found that DNN performs the best in training data, but is subject to low performance in testing data due to overfitting issue caused by high-dimensional data. The overfitting issue becomes more serious with the increase of noise level. On the other hand, FLM attains robust performance against the overfitting issue due to its simplicity and fewer parameters. However, the linear structure of FLM fails to capture complex features of the data, leading to low performance in both training data and testing data.

Simulation 2. The performance of three methods was further evaluated under different simulated functions: polynomial, logistic and linear functions. Some nonlinear regression models recommended in "Nonlinear regression models and applications in agricultural research" by Sotirios V Archontoulis and Fernando E Miguez (*Agronomy Journal* 107 (2015), no. 2, 786-798) were adapted for the evaluation.

The polynomial function was denoted as "polyno", which is described in Eq. (3.1). In addition, a "logist" function simulated in Eq. (3.2), which has logit transformation on the genetic variables. Its formula is in the following:

$$f(x; g_j, t_j, j = 1, \ldots, J) = \sum_{i=1}^{L}\sum_{j=1}^{J} c_l(1 - \exp(g_j e_l))\cos(a_l t_j + ca_l)\cos(b_l x + cb_l), \quad (3.2)$$

where $a_i$, $b_i$, $C_i \sim U[-12,12]$, $e_i \sim U[0.1,1]$, $ca_i$, $cb_i \sim U[-\pi,\pi]$. $L=30$, $J=50$. A linear setting is given by combining the above two functions. Its formula is $$f(x; g_j, t_j, j = 1, \ldots, J) = \sum_{i=1}^{L}\sum_{j=1}^{J} c_l g_j \cos(a_l t_j + ca_l)\cos(b_l x + cb_l) + c_l g_j B_{1l}(t_j) B_{2l}(x)). \quad (3.3)$$

Figure 3:
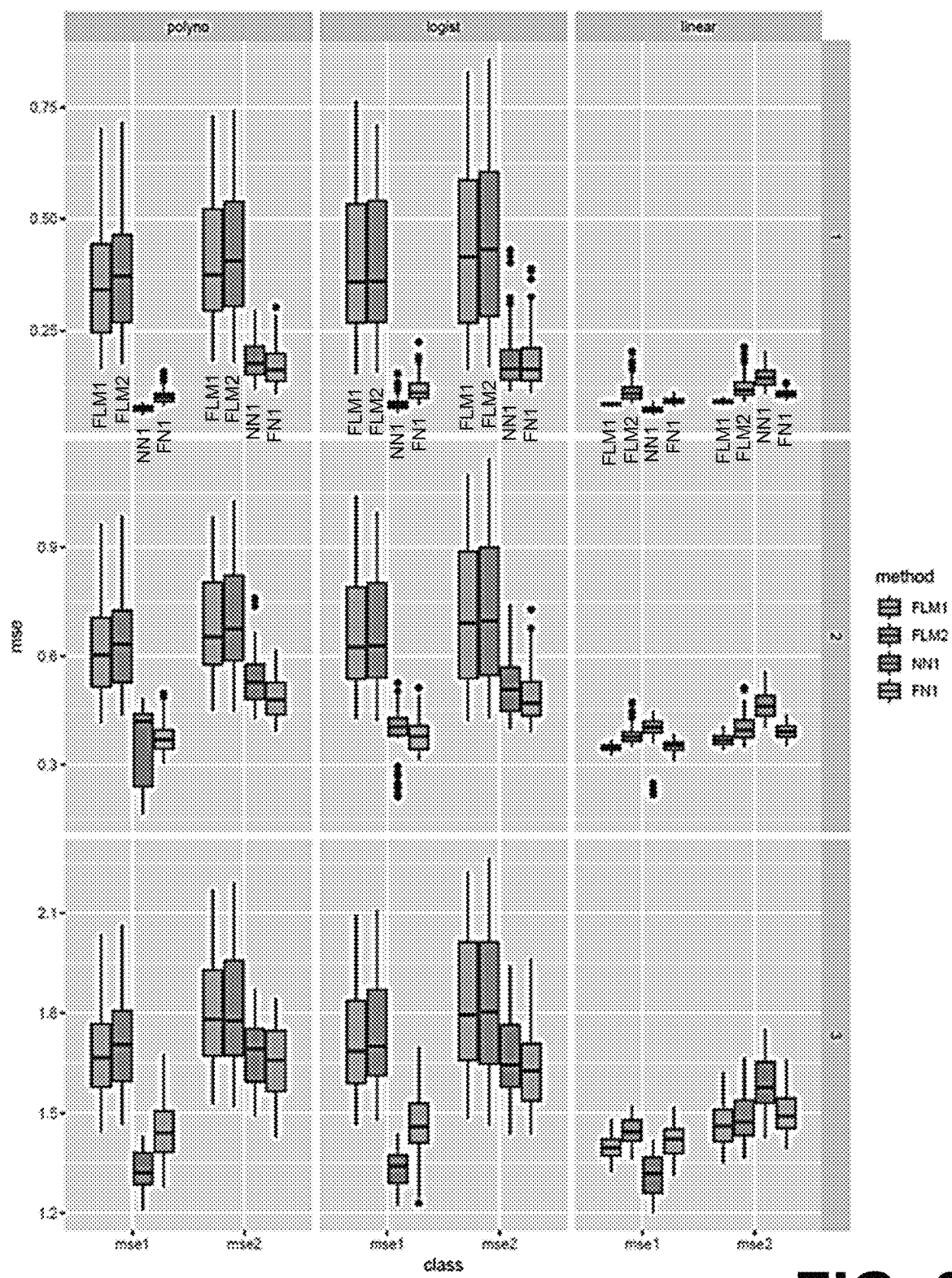
Figure 4:
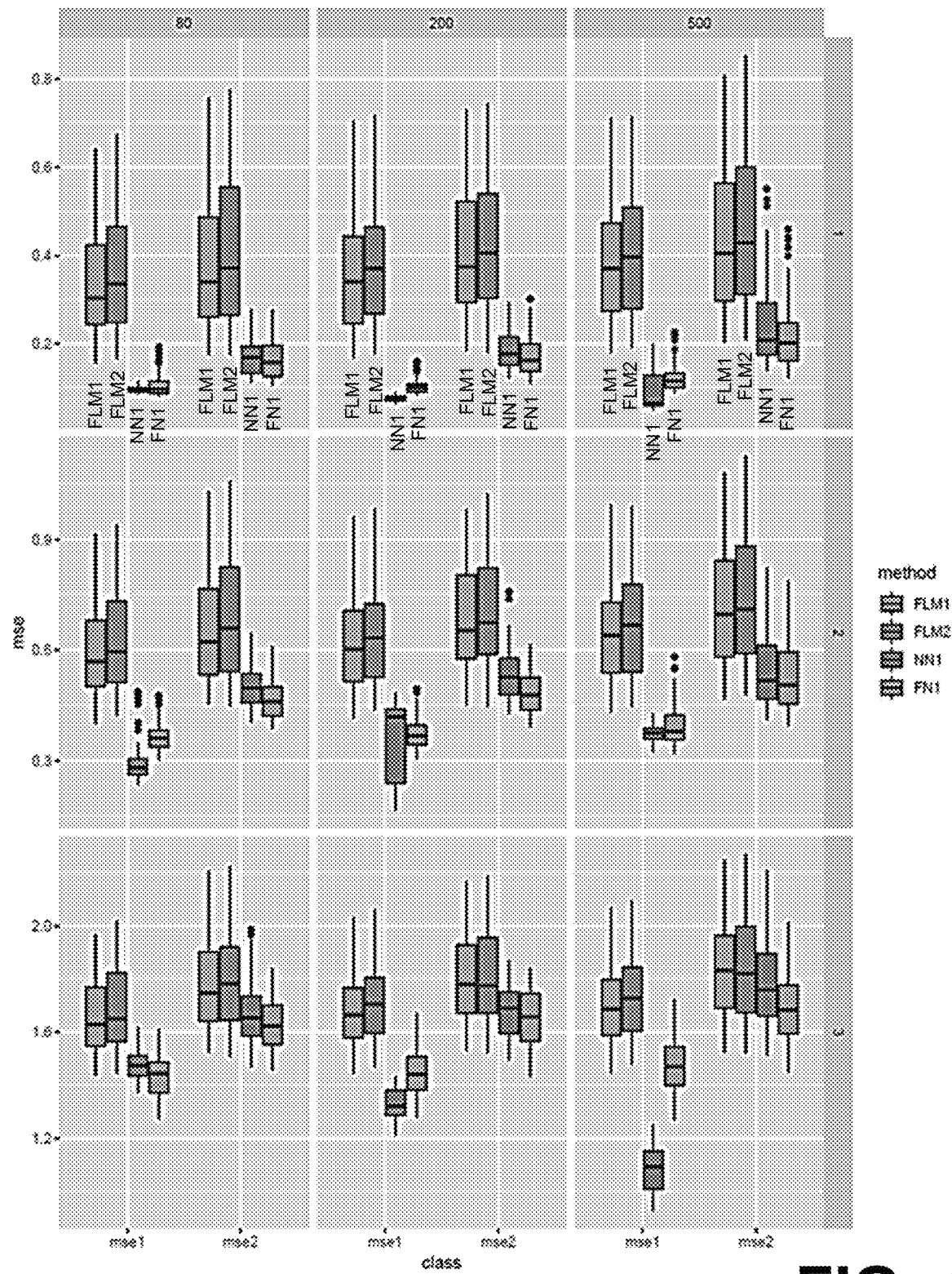

As shown in FIG. 3, overall, FDNN has better or at least comparable performance than the other two methods. As expected, FLM performs the best in linear setting, while FDNN has close performance to FLM. FDNN outperforms the other two methods in nonlinear settings. While DNN also outperform FLM in the non-linear settings, it suffers the overfitting issue due to the high dimensionality of the data.

Simulation 3. In this simulation, the performance of three methods was compared with the increased number of input variables (i.e., J=80, 200, 500 and K =20). The simulation setting is the same as the one used in simulation 2 for the polynomial phenotype, except for the number of input variables. With the number of input variable J and the noise level increase, all three methods has decreased accuracy in terms of MSE. Among three methods, FLM has most robust performance due to the linear structure it imposes. Nonetheless, such structure also limits its performance for modeling non-linear effects. While DNN is powerful for capturing non-linear effects, it suffers from overfitting issue, especially with the increase of the number of input variables and the noise level. FDNN has a good balance of bias-variance trade-off. It has the capacity of capturing non-linearity as DNN and is generally robust to increased number of input variables and noise level.

APPLICATIONS

Genetic risk prediction of nicotine dependence. Smoking and related health conditions emerged by mid-20th century and continue to represent a remarkable 21st century global burden of disease. This burden is largely driven by the nicotine dependence (ND) process that (a) drives up the count for occasions of smoking; (b) fosters escalation of dosage; and (c) generates the multiple-dose-years that account for the breadth of ND-attributable morbidity and mortality (e.g., cancers). During the last decade, substantial progress has also been made through linkage, candidate gene, and genome-wide association studies (GWAS) in identifying ND-associated genetic variants. Among the findings, the neuronal nicotinic acetylcholine receptors (nAChRs) subunit genes have attracted special interest. The nAChRs activate the release of dopamine, playing an important role in the dopaminergic reward system and the development of ND. Studies have found strong associations of the CHRNA5-CHRNA3-CHRNB4 cluster with ND. Especially, a non-synonymous coding SNVs in CHRNA5, rs 16969968, has been identified and confirmed in several large-scale studies and meta-analysis.

The use of the CHRNA5 gene and other risk factors for predicting individuals with potential high-risk of ND has been investigated, so that early intervention can be used to reduce the chance of addiction and related health conditions. De-identified samples from the Study of Addiction: Genetics and Environment (SAGE) were used for the predictive modeling analysis. The participants of the SAGE are unrelated case-control individuals selected from 3 independent studies: COGEND, COGA, and FSCD. The SAGE comprises 1321 African-American samples and 2685 Caucasian samples. The SAGE assessment plans for facets of the environment were guided by standardized interview protocols. SAGE genotyping is based on the Illumina Human 1M DNA Analysis BeadChip.

Figure 5:
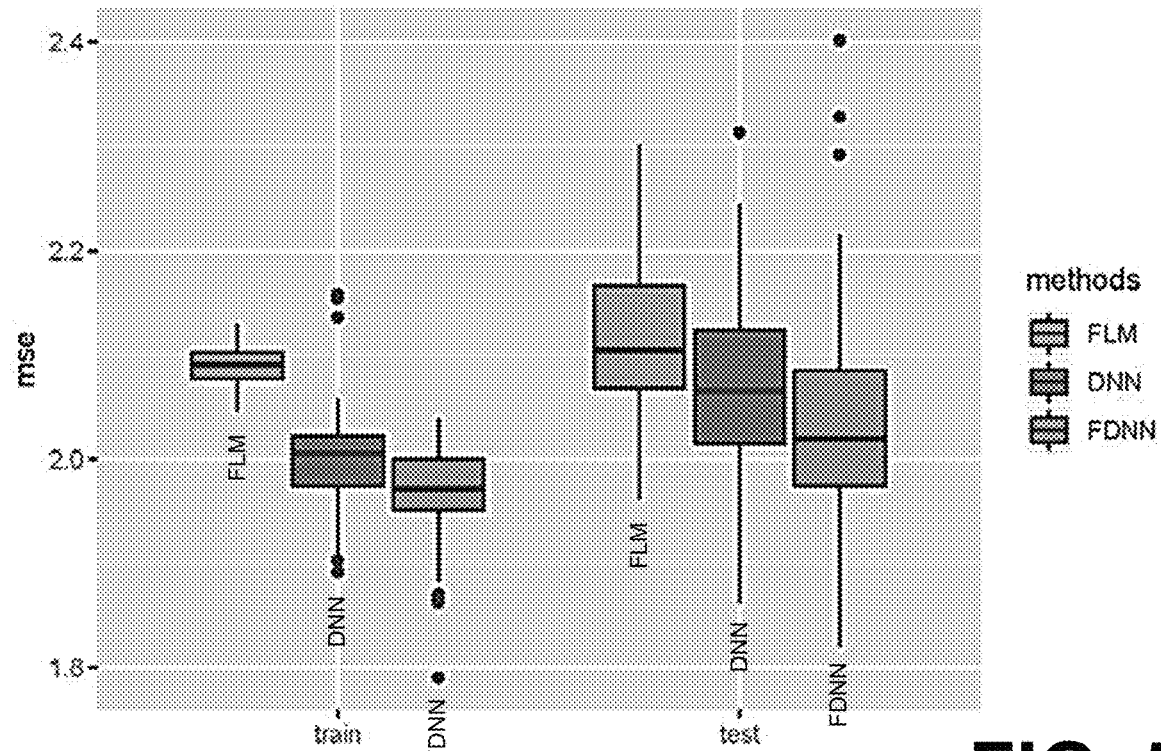
FIGS. 5 and 6 illustrate the effectiveness of DFNN in predicting nicotine dependence and Alzheimer's disease, in accordance with various embodiments of the present disclosure.

The effect of gene CHRNA5 with race, gender, and age in early predicting ND was examined, and the results are summarized in FIG. 5. In this analysis, the performance of the FDNN to predict ND using CHRNA5 was compared with FLM and DNN. As demonstrated in FIG. 5, the risk prediction model formed by FDNN attained better prediction accuracy (i.e., low prediction error) than those from FLM and DNN in terms of mean squared error (MSE). The risk prediction model built by FDNN can be further improved by considering additional genes (CYP2A6), omic data (gene expression), and environment determinants (e.g., trauma exposure), which may eventually lead to an early prediction and prevention program for nicotine addiction. In addition to ND risk prediction, FDNN can also be used in ND pharmacogenetic analyses, searching for best treatments (e.g., nicotine replacement therapy) or preventions that could be effective for each individual.

Detection of Alzheimer's disease. Accurately identifying individuals at high risk for Alzheimer's disease (AD) at an early stage is important for early AD prevention, as treatment prior to the onset of dementia can ensure intervention occurs before irreversible neuronal death. Therefore, identifying AD biomarkers can help early detect AD and promote the development of effective treatment strategies. Previous studies have shown that the hippocampus was considerably damaged before clinical AD symptoms, and therefore has been studied in AD magnetic resonance imaging (MRI) studies. Longitudinal studies have also shown decreasing hippocampal volume in AD patients.

In order to identify risk predictors related to hippocampal loss and AD, the effect of the APOE gene, a known AD gene on hippocampus volume change, was investigated over the year using the data from the Alzheimer's Disease Neuroimaging Initiative (ADNI). The ADNI study is a multisite study that assesses clinical, imaging, genetic and biospecimen biomarkers through the process of normal aging and pathologic brain aging from early Mild Cognitive Impairment to AD. It has three phases: ADNI1, ADNI GO and ADNI2. ADNI includes standardized diagnostic assessments of AD (i.e., Case vs. Control). DNA samples were obtained from ADNI participants and were sent to Illumina where non- CLIA whole genome sequencing (WGS) was performed on each sample. MR image data, PET image data (i.e., AV-45, FDG, and PIB), and clinical data (e.g., biospecimen and cognitive tests) were also collected both at the baseline and through follow-up visits. After a careful quality assessment, the joint effect of APOE gene and two important covariates (i.e., gender and length of education) on hippocampus volume change over the year was evaluated.

Figure 6:
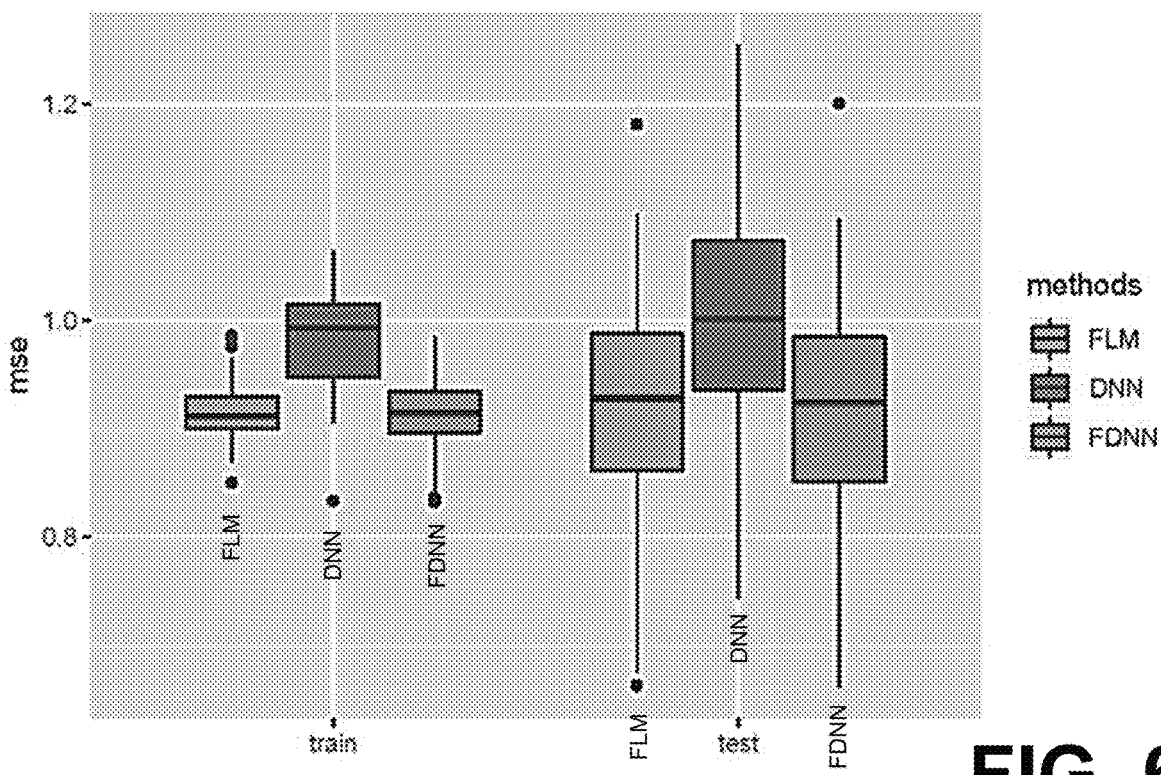

FIG. 6 illustrates the results of the analysis. It was found that APOE, gender, and length of education are related to hippocampus volume change over time and therefore can serve as AD predictors. The analysis results in FIG. 6 show that the FDNN outperformed two existing methods, FLM and DNN, in terms of prediction accuracy. The formed FDNN model can be further improved and evaluated for potential clinical use. If successful treatments become available for AD, FDNN can also be used to develop an individualized treatment strategy that can be more effective for each patient.

Figure 7:
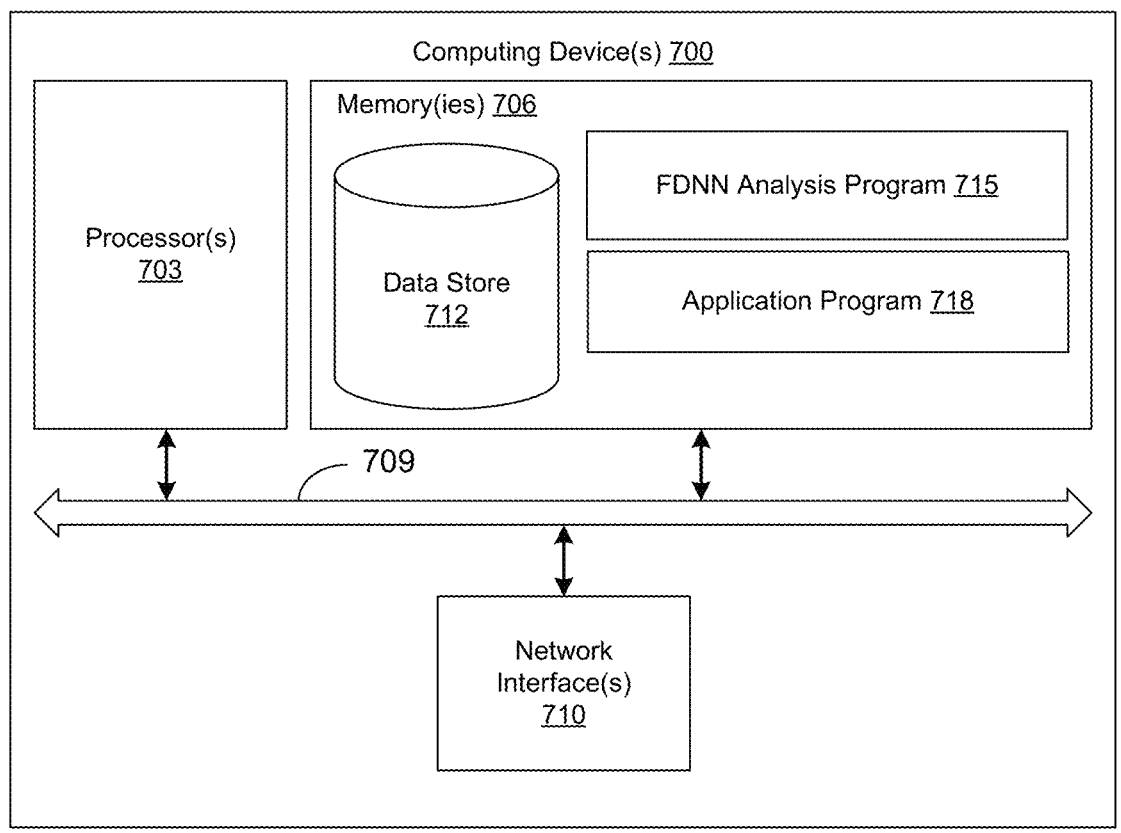
FIG. 7 is a schematic block diagram of an example of a computing device, in accordance with various embodiments of the present disclosure.

With reference to FIG. 7, shown is a schematic block diagram of a computing device 700 that can be utilized to analyze patient data for diagnosis and/or recommend treatment or prevention using the FDNN techniques. In some embodiments, among others, the computing device 700 may represent a mobile device (e.g. a smartphone, tablet, computer, etc.). Each computing device 700 includes at least one processor circuit, for example, having a processor 703 and a memory 706, both of which are coupled to a local interface 709. To this end, each computing device 700 may comprise, for example, at least one server computer or like device. The local interface 709 may comprise, for example, a data bus with an accompanying address/control bus or other bus structure as can be appreciated.

In some embodiments, the computing device 700 can include one or more network interfaces 710. The network interface 710 may comprise, for example, a wireless transmitter, a wireless transceiver, and a wireless receiver. As discussed above, the network interface 710 can communicate to a remote computing device using a Bluetooth protocol. As one skilled in the art can appreciate, other wireless protocols may be used in the various embodiments of the present disclosure.

Stored in the memory 706 are both data and several components that are executable by the processor 703. In particular, stored in the memory 706 and executable by the processor 703 are a FDNN analysis program 715, application program 718, and potentially other applications. Also stored in the memory 706 may be a data store 712 and other data. In addition, an operating system may be stored in the memory 706 and executable by the processor 703.

It is understood that there may be other applications that are stored in the memory 706 and are executable by the processor 703 as can be appreciated. Where any component discussed herein is implemented in the form of software, any one of a number of programming languages may be employed such as, for example, C, C++, C#, Objective C, Java®, JavaScript®, Perl, PHP, Visual Basic®, Python®, Ruby, Flash®, or other programming languages.

A number of software components are stored in the memory 706 and are executable by the processor 703. In this respect, the term "executable" means a program file that is in a form that can ultimately be run by the processor 703. Examples of executable programs may be, for example, a compiled program that can be translated into machine code in a format that can be loaded into a random access portion of the memory 706 and run by the processor 703, source code that may be expressed in proper format such as object code that is capable of being loaded into a random access portion of the memory 706 and executed by the processor 703, or source code that may be interpreted by another executable program to generate instructions in a random access portion of the memory 706 to be executed by the processor 703, etc. An executable program may be stored in any portion or component of the memory 706 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 706 is defined herein as including both volatile and nonvolatile memory and data storage components. Volatile components are those that do not retain data values upon loss of power. Nonvolatile components are those that retain data upon a loss of power. Thus, the memory 706 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 703 may represent multiple processors 703 and/or multiple processor cores and the memory 706 may represent multiple memories 706 that operate in parallel processing circuits, respectively. In such a case, the local interface 709 may be an appropriate network that facilitates communication between any two of the multiple processors 703, between any processor 703 and any of the memories 706, or between any two of the memories 706, etc. The local interface 709 may comprise additional systems designed to coordinate this communication, including, for example, performing load balancing. The processor 703 may be of electrical or of some other available construction.

Although the FDNN analysis program 715 and the application program 718, and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc. Such technologies are generally well known by those skilled in the art and, consequently, are not described in detail herein.

Also, any logic or application described herein, including the FDNN analysis program 715 and the application program 718, that comprises software or code can be embodied in any non-transitory computer-readable medium for use by or in connection with an instruction execution system such as, for example, a processor 703 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system.

The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

Further, any logic or application described herein, including the FDNN analysis program 715 and the application program 718, may be implemented and structured in a variety of ways. For example, one or more applications described may be implemented as modules or components of a single application. Further, one or more applications described herein may be executed in shared or separate computing devices or a combination thereof. For example, a plurality of the applications described herein may execute in the same computing device 700, or in multiple computing devices in the same computing environment. Additionally, it is understood that terms such as "application," "service," "system," "engine," "module," and so on may be interchangeable and are not intended to be limiting.

APPENDIX A: Solutions of FLM

Solution to Eq. (2.1). In the real world, no true functions but rather discrete points are recorded at $t_i$, j=1, ..., p. In order words, the genetic variants is $G_i(t_i)$, which can be denoted $a_{ij}$. Therefore, the model can be transformed into the beta-smooth function:

$$\hat{y}_i = \theta_0 + Z_i\theta + \sum_{j=1}^{p} G_{ij}\beta(t_j),  \quad (A.1)$$

By using pre-specified basis functions $\beta_k(t)$, k=1, ..., K (e.g., B-spline basis functions), $\beta(t)$ can be further expanded as $$\beta(t) = \sum_{k=1}^{K} w_k \beta_k(t),$$

and FLM can be rewritten as, $$\hat{y}_i = \theta_0 + Z_i\theta + \sum_{j=1}^{p} G_{ij}\left(\sum_{k=1}^{k} w_k\beta_k(t_j)\right)$$

$$= \theta_0 + Z_i\theta + \sum_{k=1}^{k} w_k\left(\sum_{j=1}^{p} G_{ij}\beta_k(t_j)\right),$$

$$= \theta_0 + Z_i\theta + \sum_{k=1}^{k} w_k d_{ik}$$

$$= \theta_0 + Z_i\theta + D_i w$$

where $$d_{ik} = \sum_{k=1}^{p} G_{ij}\beta_k(t_j),$$

$w=(w_1, ..., w_k)^T$ and $D_i=(d_{i1}, ..., d_{iK})^T$. The FLM of Eq. (2.1) is transformed to a linear model:

$$\hat{Y}=X\theta+Dw, \quad (A.2)$$

where $X=(1_n,Z)$, $Z=(Z^T_1, ..., Z^T_n)^T$, $\theta=(\theta_0, \theta^T)^T$. $1_n$ refers to a column vector whose elements are always 1 and length is n.

The objective function to minimize is:

$$R(w, \Theta) = (\hat{Y} - Y)^T(\hat{Y} - Y) + \lambda\int(\beta''(t))^2 dt = (\hat{Y}-Y)^T(\hat{Y}-Y) + \lambda w^T Pw$$

Hence, the following solution can be obtained.

$$\hat{w}=(D^T(I-X(X^TX)^{-1}X^T)D+\lambda P)^{-1}D^T(I-X(X^TX)^{-1})Y \quad (A.3)$$

$$\hat{\theta}=(X^TX)^{-1}X^T(Y-D\hat{w}). \quad (A.4)$$

Solution to Eq. (2.2). No existing analytical method is available to the above model if no restrictions are imposed. The commonly used restriction $s_{ij}=s_{i'j}$, $\forall i,,i'$ can be adapted. Without loss of generality, we use $s_j$, $\varepsilon_{ij}$ to denote $s_{ij}$ and $\varepsilon_i(s_{ij})$. Then the model can be rewritten as:

$$Y_{ij}=Y(s_j)=Z_i\theta+\alpha_0(s_j)+\int\alpha(s_j,t)G^i(t)dt+\varepsilon_{ij}, \quad (A.5)$$

which can be further generalized by assuming the covariate coefficient vector $\theta$ as a functional coefficient vector, i.e., $$Y_{ij}=Z_i\theta(s_j)+\alpha_0(s_j)+\int\alpha(s_j,t)G_i(t)dt+\varepsilon_{ij}. \quad (A.6)$$

where $\theta(s)=(\theta_1(s), ..., \theta_m(s))$.

By adding another basis function $\alpha_l(s)$, l=1, ..., L, $\alpha_0(s)$ can be replaced by $$\sum_{l=1}^{L} c_l\alpha_l(s)$$

and $\alpha(s, t)$ by $$\sum_{k=1}^{K}\sum_{l=1}^{L} W_{kl}\alpha_l(s)\beta_k(t).$$

Denote $d_{ik}=\int G_i(t)\beta_k(t)dt$, in which the integration could be defined.

To denote the bivariate function $\alpha(s, t)$, two basis function systems are needed, $\{\beta_{k(d)}^{(d)}d\varepsilon\{0,1\}, k_d \in\{1, ..., \}\}$. Then, $$\alpha_0(s) = \sum_{k^{(1)}=1}^{I^{(1)}} b_{k(1)}^{(1)} \beta_{k(1)}^{(1)}(s) \quad (A.7)$$

$$\alpha(s,t) = \sum_{k^{(1)}=1}^{I^{(1)}} \sum_{k^{(0)}=1}^{I^{(0)}} W_{k^{(0)}k^{(1)}} \beta_{k^{(0)}}^{(0)}(t) \beta_{k^{(1)}}^{(1)}(s). \quad (A.8)$$

The package provided by "Penalized function-on-function regression" by Andrada E Ivanescu, Ana-Maria Staicu, Fabian Scheipl, and Sonja Greven (*Computational Statistics* 30 (2015), no. 2, 539-568) based on the REML method can be used to solve W, b and θ by minimizing the L2 error.

APPENDIX B: Forward Propagation

In practice, integration can be approximated by numeric integration in the form of summation to simplify the computation. In the scenario of the model, all functions are on the support of the interval [0,1]. If evenly distributed points $t_1, t_2, \ldots, t_2, \ldots, t_m$ are chosen, a naive integration for $f(t)$ is $$\int f(t)dt = \sum_{j=1}^{m} f(t_j)/m. \quad (B.1)$$

Denote that:

$$\alpha_0^{(d)}(t^{(d)}) = \sum_{k^{(d)}=1}^{I^{(d)}} b_{k^{(d)}}^{(d)} \beta_{k^{(d)}}^{(d)}(t^{(d)}) \quad (B.2)$$

where $\{\beta_k^{(d)}, k=1, \ldots, I^{(d)}\}$ is the basis system.

The functional notation can be rewritten in a matrix form, $$B^{(d)} = [\beta_{k^{(d)}}^{(d)}(t_j^{(d)})]_{j=1,k^{(d)}=1}^{m^{(d)},I^{(d)}} \quad (B.4)$$

$$X^{(d)} = [X_i^{(d)}(t_j^{(d)})]_{i=1,j=1}^{n,m^{(d)}}. \quad (B.5)$$

Therefore, the forward propagation algorithm can be written as the following:

$$D^{(d)} = X^{(d-1)} B^{(d-1)}/m^{(d-1)} \quad (B.6)$$

$$C^{(1)} = D^{(1)} W^{(1)} + 1_{n,1} b^{(1)} + ZC \quad (B.7)$$

$$C^{(d)} = D^{(d)} W^{(d)} + 1_{n,1} b^{(d)} d > 1 \quad (B.8)$$

$$X^{(d)} = \sigma^{(d)}(C^{(d)} B^{(d)T}). \quad (B.9)$$

As compared with the DNN model, the FDNN model reduces to a traditional neural network when each matrix of basis B is diagonal matrix. In other words, the neural network can be viewed as a special case of the FDNN method.

APPENDIX C: Back Propagation

The back propagation algorithm can be derived from the traditional neural network method. First, define the loss function L(y, ŷ) and risk function R(W, b), where $$L(y, \hat{y}) = (y - \hat{y})^2 \quad (C.1)$$

$$R(W, b) = \sum_{i,j} L(y(t_{ij}), \hat{y}(t_{ij})). \quad (C.2)$$

To avoid overfitting, a penalty J(W, b) is added to the risk function, where $$J(W, b) = \sum_{d=1}^{D} J^{(d)}(W^{(d)}, b^{(d)}) \quad (C.3)$$

$$J^{(d)} = \int\int \left[\lambda^{(d)}\left(\frac{\partial^2 \alpha^{(d)}}{\partial t^{(d)2}}\right)^2 + \lambda^{(d-1)}\left(\frac{\partial^2 \alpha^{(d)}}{\partial t^{(d-1)2}}\right)^2\right] dt^{(d)} dt^{(d-1)}, \quad (C.4)$$

in which λ is a hyperparameter selected by validation.

Gradient decent is applied to estimate the weight function coefficients. The recursive process stops when $R^{(r)}$ converges.

$$O^{(r)} = R(W^{(r)}, b^{(r)}) + J(W, b) \quad (C.5)$$

$$W^{(r+1)} = W^{(r)} - \gamma \frac{\partial O^{(r)}}{\partial W^{(r)}} \quad (C.6)$$

$$b^{(r+1)} = b^{(r)} - \gamma \frac{\partial O^{(r)}}{\partial b^{(r)}}, \quad (C.7)$$

where γ is determined by the Adadelta method which is introduced in *Adadelta: an adaptive learning rate method* by Matthew D Zeiler (arXiv preprint arXiv: 1212.5701, 2012). The deductions of derivatives involve matrices, functions and trace. Two lemmas are given below to simplify the calculation of derivatives.

Lemma C.1. Having function σ: $\mathbb{R} \to \mathbb{R}$ applied to matrix elementwisely, $f: \mathbb{R}^{m \times n} \to \mathbb{R}$ that maps matrix to scalar. X, A, B are matrices with proper dimensions and A=σ(B).

If $\frac{\partial f(X)}{\partial A} = D$, then $\frac{\partial f(X)}{\partial B} = D \circ \sigma'(B)$ Proof.

$$\frac{f(X)}{B_{ij}} = \frac{f(X)}{\sigma(A_{ij})} \frac{A_{ij}}{B_{ij}} = D_{ij} \sigma'(B_{ij}) = (D \circ \sigma'(B))_{ij} \square$$

Lemma C.2. Having function $f: \mathbb{R}^{m \times n} \to \mathbb{R}$ that maps matrix to scalar. A, C are square matrices and Y=ABC.

If $\frac{\partial f(X)}{\partial Y} = D$, then $\frac{\partial f(X)}{\partial B} = A^T D C^T$ Proof $$\frac{\partial f(X)}{\partial B_{ij}} = \sum_{k,l} \left(\frac{\partial f(X)}{\partial ABC}\right)_{k,l} \frac{\partial (ABC)_{k,l}}{\partial B_{ij}}$$

$$= \sum_{k,l} D_{kl} A_{ki} C_{jl}$$

$$= \sum_{k,l} A_{ik}^T D_{kl} C_{lj}^T$$

$$= (A^T D C^T)_{ij} \square$$

Denoting $$M^{(d)} = \frac{\partial R(W, b)}{\partial C^{(d)}},$$

then:

$$\frac{\partial R(W, b)}{\partial b^{(d)}} = 1_{1,n} M^{(d)} \quad (C.8)$$

$$\frac{\partial R(W, b)}{\partial W^{(d)}} = \left(X^{(d-1)} B^{(d-1)}\right)^T M^{(d)} / m^{(d-1)}. \quad (C.9)$$

For the last layer, $\sigma^{(D)}$ is a linear function, $\hat{Y} = C^{(D)} B^{(D)T}$, and:

$$\frac{\partial R(W, b)}{\partial \hat{Y}} = \frac{\partial \sum_{i,j} (\hat{y}_{ij} - y_{ij})^2}{\partial \hat{Y}} = = 2(\hat{Y} - Y)$$

$$M^{(D)} = 2(\hat{Y} - Y) B^{(D)}.$$

For the other layers, $$C^{(d+1)} = \left(X^{(d)} B^{(d)}/m^{(d)}\right) W^{(d+1)} + 1_{n,1} b^{(d+1)}$$

$$= \sigma^{(d)} \left(C^{(d)} B^{(d)T}\right) B^{(d)} W^{(d+1)}/m^{(d)} + 1_{n,1} c^{(d+1)}.$$

By lemmas C.1 and C.2, we have:

$$\frac{\partial R(W, b)}{\partial \sigma^{(d)} \left(C^{(d)} B^{(d)T}\right)} = M^{(d+1)} W^{(d+1)T} B^{(d)T}/m^{(d)} \quad (C.10)$$

$$\frac{\partial R(W, b)}{\partial \left(C^{(d)} B^{(d)T}\right)} = M^{(d+1)} W^{(d+1)T} B^{(d)T} \circ \sigma' \left(C^{(d)} B^{(d)T}\right)/m^{(d)}$$

$$M^{(d)} = \left[\left(M^{(d+1)} W^{(d+1)T} B^{(d)T} \circ \sigma' \left(C^{(d)} B^{(d)T}\right)\right)\right] B^{(d)}/m^{(d)}$$

$$P_o^{(d)} = \left[\int \beta_i^{(d)}(t^{(d)}) \beta_j^{(d)}(t^{(d)}) dt^{(d)}\right]_{i=1,j=1}^{I^{(d)}, I^{(d)}}$$

$$P_2^{(d)} = \left[\int \beta_i^{(d)''}(t^{(d)}) \beta_j^{(d)''}(t^{(d)}) dt^{(d)}\right]_{i=1,j=1}^{I^{(d)}, I^{(d)}}. \quad (C.11)$$

$$J^{(d)} = \int\int\left[\lambda^{(d)} \left(\frac{\partial^2 \alpha^{(d)}}{\partial t^{(d)2}}\right)^2 + \lambda^{(d-1)} \left(\frac{\partial^2 \alpha^{(d)}}{\partial t^{(d-1)2}}\right)^2\right] dt^{(d)} dt^{(d-1)} + \lambda^{(d)} \int \left(\frac{\partial^2 \alpha_0^{(d)}}{\partial t^{(d)2}}\right)^2 dt^{(d)} \quad (C.12)$$

$$= tr\left(\lambda^{(d)} P_0^{(d-1)} W^{(d)} P_2^{(d)} W^{(d)'} + \lambda^{(d-1)} P_o^{(d)} W^{(d)'} P_2^{(d-1)} W^{(d)}\right) + tr\left(\lambda^{(d)} b^{(d)} P_2^{(d)} b^{(d)'}\right)$$

$$\frac{\partial J^{(d)}}{\partial W^{(d)}} = 2\lambda^{(d)} P_0^{(d-1)} W^{(d)} P_2^{(d)} + 2\lambda^{(d-1)} P_2^{(d-1)} W^{(d)} P_0^{(d)}$$

$$\frac{\partial J^{(d)}}{\partial b^{(d)}} = 2\lambda^{(d)} b^{(d)} P_2^{(d)}. \quad (C.13)$$

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

The term "substantially" is meant to permit deviations from the descriptive term that don't negatively impact the intended purpose. Descriptive terms are implicitly understood to be modified by the word substantially, even if the term is not explicitly modified by the word substantially.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

Therefore, at least the following is claimed:

1. A method for risk prediction using high-dimensional omic data, comprising:

training, by at least one computing device, a functional deep neural network (FDNN) with a training set of omic data to produce a trained FDNN model, the trained FDNN model comprising a series of basis functions as a plurality of layers that capture complexity between the omic data with disease phenotypes after training, the training set of omic data comprising biomarkers applied as inputs to the FDNN and one or more phenotypes, the trained FDNN model configured to provide output indications in a standardized format;

obtaining, by the at least one computing device, omic data corresponding to an individual, the omic data comprising a multi-level omic profile from the individual stored in a database;

determining, by the at least one computing device, a likelihood of a condition associated with a disease based upon output indications of the FDNN corresponding to the one or more phenotypes, the output indications based upon analysis of the omic data comprising the multi-level omic profile from the individual by the trained FDNN;

identifying, by the at least one computing device, a treatment for the individual based at least in part upon the likelihood of the condition; and generating, by the at least one computing device, an indication of the treatment for rendering on a networked computing device, the indication of treatment transmitted to all authorized medical or clinical personnel over a network for real time access via networked computing devices.

2. The method of claim 1, wherein a first layer of the plurality of layers comprises a univariate function and remaining layers of the plurality of layers comprise a bivariate function.

3. The method of claim 1, wherein the training set of omic data comprises risk predictors related to the one or more phenotypes, the risk predictors including biomarkers or established risk predictors.

4. The method of claim 3, wherein the one or more phenotypes comprise disease diagnostic assessments, multiple correlated phenotypes, or high-dimensional phenotypes.

5. The method of claim 4, wherein the high-dimensional phenotypes comprise biomarkers or neuroimaging data.

6. The method of claim 1, wherein the plurality of layers of the FDNN are built via functional linear models with functional coefficients as weights in individual layers.

7. The method of claim 6, wherein the plurality of layers of the FDNN adopts a penalty on a second-order derivative of the basis functions to ensure smoothness of the basis functions.

8. The method of claim 1, wherein weights and biases in the FDNN are functions, and the FDNN takes an integral of functional coefficients in individual layers.

9. A system for risk prediction using high-dimensional omic data, comprising:

at least one computing device comprising processing circuitry including a processor and memory; and a FDNN analysis program that, when executed by the processing circuitry, cause the at least one computing device to:

obtain an omic profile of an individual, the omic profile comprising a multi-level omic profile from the individual stored in a database;

determining a likelihood of a condition associated with a disease based upon output indications of a functional deep neural network (FDNN) corresponding to one or more phenotypes, the output indications based upon analysis of omic data comprising the multi-level omic profile by the FDNN, where the FDNN was trained with a training set of omic data to produce a trained FDNN model, the trained FDNN model comprising a series of basis functions as a plurality of layers that capture complexity between the omic data with disease phenotypes, the trained FDNN model configured to provide the output indications in a standardized format;

providing a treatment identified for the individual based at least in part upon the likelihood of the condition; and generating an indication of the treatment for rendering on a networked computing device or another computing device, the indication of treatment transmitted to all authorized medical or clinical personnel over a network for real time access via networked computing devices.

10. The system of claim 9, wherein the training set of omic data comprising biomarkers applied as inputs to the FDNN and the one or more phenotypes.

11. The system of claim 10, wherein the training set of omic data comprises risk predictors related to the one or more phenotypes, the risk predictors including biomarkers or established risk predictors.

12. The system of claim 11, wherein the one or more phenotypes comprise disease diagnostic assessments, multiple correlated phenotypes, or high- dimensional phenotypes.

13. The system of claim 12, wherein the high-dimensional phenotypes comprise multi-level omic or neuroimaging data.

14. The system of claim 9, wherein a first layer of the plurality of layers comprises a univariate function and remaining layers of the plurality of layers comprise a bivariate function.

15. The system of claim 9, wherein the plurality of layers of the FDNN are built via functional linear models with functional coefficients as weights in individual layers.

16. The system of claim 15, wherein the plurality of layers of the FDNN adopts a penalty on a second-order derivative of the basis functions to ensure smoothness of the basis functions.

17. The system of claim 9, wherein weights and biases in the FDNN are functions, and the FDNN takes an integral of functional coefficients in individual layers.

* * * * *